United States Patent [19]

Dauben et al.

[11] 4,298,752

[45] Nov. 3, 1981

[54] CYCLOADDUCT PRECURSORS OF CANTHARIDIN AND METHOD

[75] Inventors: William G. Dauben, Berkeley; Carl R. Kessel, Union City, both of Calif.; Kazuo H. Takemura, Omaha, Nebr.

[73] Assignee: Regents of the University of California, Berkeley, Calif.

[21] Appl. No.: 188,883

[22] Filed: Sep. 19, 1980

[51] Int. Cl.³ .................................. C07D 493/18
[52] U.S. Cl. .............................. 549/42; 260/346.3; 260/346.6
[58] Field of Search .................. 260/346.3, 346.6; 549/42

[56]  References Cited

PUBLICATIONS von Bruchhausen, F. and Bersch, H. W., *Arch. Pharm.* 266, 697–702 (1928).
Diels, O. and Alder, K., *Ber.*, 62, 554–562 (1929).
Ziegler, K., et al., *Ann*, 551, 1–79 (1942).
Paranjape, K. D., et al., *Proc. Indian Acad, Sci.*, 19A, 385–388 (1944).
Stork, G., et al., *J. Am. Chem. Soc.*, 75, 384–392 (1953).
Stork, G., et al., *J. Am. Chem. Soc.*, 73, 4501 (1951).
Baker, B. R., et al., *J. Org. Chem.*, 13, 123–133 (1948).
Schenck, O. G. and Wirtz, *Naturwissenschaften*, 40, 581 (1953).
Dauben, W. G. and Drabbenhoft, H. O., *J. Am. Chem. Soc.*, 1992–1993 (1976).
Rimmelin, J., et al. *Bull Soc. Chim. Fr.*, 461–464 (1978).
Gladysz, J. A., *Chemtech*, 372–377 (1979).

*Primary Examiner*—Richard Raymond
*Attorney, Agent, or Firm*—Phillips, Moore, Weissenberger, Lempio & Majestic

[57]  ABSTRACT

Novel cycloadducts are provided which may be formed between furan and 2,5-dihydrothiophene-3,4-dicarboxylic anhydride at elevated pressure. One of these cycloadducts is useful in a synthesis of cantharidin. Another yields a novel isomeric cantharidin.

16 Claims, No Drawings

CYCLOADDUCT PRECURSORS OF CANTHARIDIN AND METHOD

The Government has rights in this invention pursuant to Grant No. 78-04811 awarded by the National Science Foundation.

DESCRIPTION

BACKGROUND OF THE INVENTION

1. Field of the Invention

This invention relates to cycloadducts formed with furan, and more particularly to the synthesis of Cantharidin.

2. Prior Art

Cantharidin is found in various species of catharides beetles, such as *cantharis vesicatoria* (commonly known as Spanish Fly), and has the structure

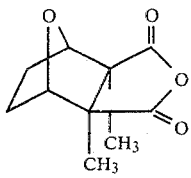

Notwithstanding its notoriety as a putative aphrodisiac, cantharidin has found various commercial applications, for example in the removal of benign skin growths such as warts. Cantharidin is presently commercially obtained by purification from natural sources.

Cantharidin has been an enticing but elusive target for total synthesis. Early attempts at a [4+2] cycloaddition between dimethylmaleic anhydride and furan failed, for example as reported by Otto Diels and Kurt Alder, BER., 62 (1929) 554–562. To date, there has been no commercially feasible, synthetic approach to the production of cantharidin, although three different methods for synthesis have been reported. However, these methods have involved a number of steps, have produced low yields of cantharidin, and have not proven to be commercially feasible.

Accordingly, a good and general method for synthesizing cantharidin in high yield has been lacking.

SUMMARY OF THE INVENTION

The present invention is concerned with cycloadducts formed between furan and a particular type of dienophile, and a method for synthesizing cantharidin in high yield therefrom.

In one aspect of the present invention, a method of forming a cycloadduct comprises the steps of providing a dienophile having a maleic anhydride nucleus and a bridge substituted thereon which includes a sulfur moiety. The dienophile is contacted with furan to form a reaction solution. The reaction solution is pressurized to cause a cycloaddition between the dienophile and furan.

A novel cycloadduct resulting from the pressurizing has the structure

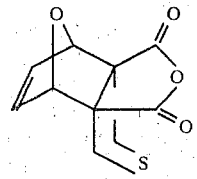

In another aspect of the present invention, the novel cycloadduct may be desulfurized and the carbon-carbon double bond saturated to form cantharidin in a one-step procedure; alternatively, the novel cycloadduct may first be hydrogenated to form another cycloadduct.

In the best mode contemplated for practice of the present invention, a particular one dienophile is utilized to form the novel cycloadduct. The novel cycloadduct need not be isolated following its formation from the pressurizing step, but instead may be contacted with a metallic catalyst to produce cantharidin. Cantharidin may then be isolated in excellent yield with respect to the precursor dienophile.

Other aspects and advantages of the invention will become apparent from the following description and appended claims.

DETAILED DESCRIPTION OF THE PREFERRED EMBODIMENTS

Attempts to utilize furan as a diene and dimethylmaleic anhydride as a dienophile in a Diels-Alder type reaction have proven unsuccessful.

It is believed that the failure of dimethylmaleic anhydride to add to furan is a result of both electronic and steric factors. That is, it is believed that the electron donating methyl groups of dimethylmaleic anhydride decrease its dienophilicity, and that the extra crowding in the transition state given by these same methyl groups further reduces its reactivity. Additionally, furan is known to be a poor Diels-Alder diene due to its aromaticity, and various cycloaddition products which have been derived from furan have been found to be generally susceptible to thermal cycloreversion. Although it has been reported that extremely high pressures (above about $1 \times 10^6$ kPa) might facilitate some Diels-Alder reactions of furan, it has been found that dimethylmaleic anhydride will not add to furan even at pressures up to $4 \times 10^6$ kPa.

The present invention provides a method wherein a particular type of dienophile forms a cycloadduct with furan when a solution including the dienophile and furan is pressurized.

The suitable type of dienophile for cycloaddition with furan in accordance with the present invention has a maleic anhydride nucleus and a bridge substituted thereon. The suitable dienophile is of the structure illustrated by FIG. 1, below.

FIG. 1

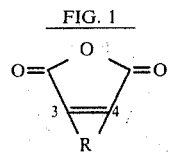

wherein R represents the bridge. This suitable dienophile shall sometimes hereinafter be referred to as the "FIG. 1 dienophile".

The bridge functions to reduce an electron density of the carbon-carbon double bond of the maleic anhydride nucleus located between the 3 and 4 carbons thereof. More particularly, the bridge includes a sulfur moiety.

The sulfur moiety is not connected directly to the 3,4 carbons defining the carbon-carbon double bond, but rather is bonded between hydrocarbon spacer arms. These spacer arms are preferably each —CH$_2$— when the use of the dienophile is ultimately to form cantharidin, or an isomeric cantharidin (as further described hereinafter).

The sulfur moiety of the bridge may be in the form of a sulfide, sulfoxide or sulfone, and preferably the sulfur moiety is a sulfide. The most preferred dienophile for practice of the present invention in forming a cycloadduct is 2,5-dihydrothiophene-3,4-dicarboxylic anhydride. This compound is known, and has the structure illustrated by FIG. 2, below.

FIG. 2

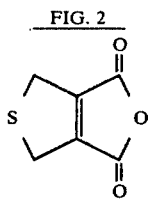

The compound illustrated by FIG. 2, above, shall hereinafter sometimes be referred to as the "FIG. 2 dienophile".

A method for forming a cycloadduct in accordance with the present invention includes contacting the FIG. 1 dienophile with furan to form a reaction solution. When the FIG. 2 dienophile is contacted with furan a reaction solution is formed and a cycloaddition therebetween is caused upon the utilization of high pressure to form two new cycloadducts. These two new cycloadducts are isomers having the structures represented by FIGS. 3 and 4, below.

FIG. 3

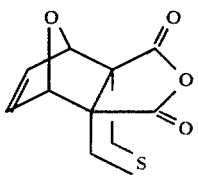

FIG. 4 —continued

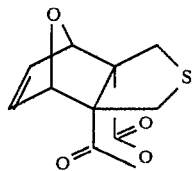

These two cycloadducts shall sometimes hereinafter be referred to as the "FIG. 3 cycloadduct" and the "FIG. 4 cycloadduct". Characterization data for these two cycloadduct isomers are tabulated in Table I, below.

TABLE I

| FIG. 3 Cycloadduct Isomer | FIG. 4 Cycloadduct Isomer |
|---|---|
| m.p. 112–113° C. (acetone-hexane) | m.p. 125–126° C. (chromatograph) |
| IR (CDCl$_3$) 1885,1780,1255,980 cm$^{-1}$ | IR (CDCl$_3$) 1847,1780,1172,967 cm$^{-1}$ |
| NMR (CDCl$_3$, TMS) δ 2.68(d,2,J = 12.5), 3.17 (d,2,J = 12.5), 5.15 (m,2), 6.67(m,2) | NMR (CDCl$_3$,TMS) δ 3.01 (d,2,J = 12.5) 3.41 (d,2,J = 12.5), 4.94(br.s,2), 6.58 (br.s,2) |
| Anal. calcd for C$_{10}$H$_8$O$_4$S: C,53.56;H, 3.60; S, 14.30 | Anal. calcd for C$_{10}$H$_8$O$_4$S: C,53.56; H, 3.60; S, 14.30 |
| Found: C, 53.55; H, 3.75; S, 14.18 | Found: C, 53.59; H, 3.70; S, 14.31 |

The contacting may be between the Figure dienophile and furan, neat, to form the reaction solution or may include the presence of a suitable solvent for the dienophile to form the reaction solution. Various organic solvents are suitable for the FIG. 1 dienophile in the contacting step. For example, the most preferred FIG. 2 dienophile has a solubility of about 60 mg/mL in CH$_2$Cl$_2$ and a solubility about 120 mg/mL in either CH$_3$COCH$_3$ or CH$_3$CN, and these solvents are suitable for forming the reaction solution and subsequent pressurization when the FIG. 2 dienophile is provided; however, at pressures of about 15×10$^5$ kPa, methylene chloride is preferred as the solvent for the FIG. 2 dienophile because relatively large amounts of side reaction products tend to be formed with acetonitrile and acetone.

In the inventive method, the reaction solution is pressurized to cause formation of at least one cycloadduct. Such pressurization is preferably at least about 1×10$^5$ kPa, more preferably at least about 4×10$^5$ kPa. At a pressure of at least about 1×10$^5$ kPa, the pressurization equipment employed can have a larger useable volume than, for example, pressures of about 15×10$^5$ kPa; however, the relatively lower (but still elevated) pressures require a longer period of time to achieve the cycloaddition reaction.

Table II, below, illustrates data from practice of the inventive method in forming the FIG. 3 and FIG. 4 cycloadducts (using 1.2 eq. furan with respect to 2,5-dihydrothiophene-3,4-dicarboxylic anhydride).

TABLE II

| Solvent | Conc. dienophile (M/L) | Pressure (× 10⁵kPa) | Time (h) | Conversion[a] (%) | Product Ratio[a,b] (FIG. 3 cycloadduct: FIG. 4 cycloadduct) |
|---|---|---|---|---|---|
| (furan, neat) | 0.45 | 1 | 94 | 79 | 78:22 |
| CH₂Cl₂ | 0.26 | 15 | 6 | 100 | 85:15 |
| " | 0.26 | 8 | 42 | 79 | 85:15 |
| " | 0.26 | 4 | 88 | 41 | 80:20 |
| " | 0.26 | 1 | 94 | 8 | not determined |
| CH₃COCH₃ | 0.45 | 15 | 24 | c | |
| " | 0.45 | 8 | 42 | 81 | 85:15 |
| " | 0.45 | 4 | 88 | 49 | 85:15 |
| CH₃CN | 0.45 | 15 | 24 | c | |
| " | 0.45 | 8 | 42 | 64[d] | 85:15 |
| " | 0.45 | 4 | 88 | 57 | 85:15 |

[a]Determined by NMR spectroscopy.
[b]Unless otherwise noted, no other products were observable by NMR spectroscopy.
[c]Quantitative analysis of reaction mixture not possible by NMR spectroscopy due to poly-Diels-Alder products.
[d]Some diacid formed.

Pressurization may be conducted with conventional high pressure equipment, such as for example a piston and cylinder device. The formation of the FIGS. 3 and 4 cycloadduct isomers, as represented by the data of Table II, is generally illustrated by Reaction Scheme, I, below.

Reaction Scheme I

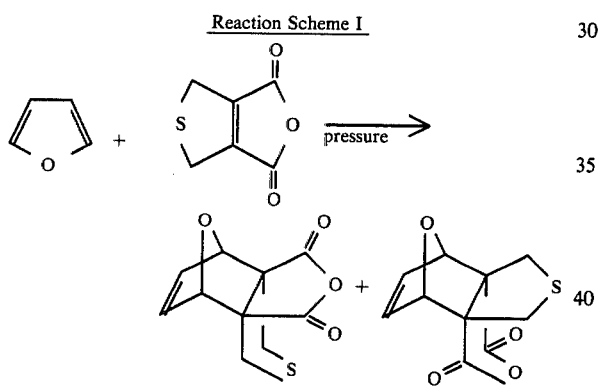

The FIG. 3 cycloadduct is useful as a precusor for producing cantharidin by utilizing means for saturating the carbon-carbon double bond and desulfurizing. Similarly, the FIG. 4 cycloadduct is useful as a precursor for producing an isomeric cantharidin (further described hereinafter) by utilizing means for saturating the carbon-carbon double bond and desulfurizing.

In the best mode contemplated for producing cantharidin such means is preferably by contacting a mixture of these cycloadducts with a suitable catalyst in a one step procedure. The one step contacting is preferred due to efficiency and higher ultimate yield of cantharidin and shall next be more fully described.

The FIG. 3 cycloadduct is preferably contacted with a metallic catalyst sufficient to perform a one-step desulfurization and saturation of the carbon-carbon double bond, so as to form cantharidin as a product therefrom. In this one-step procedure, the FIG. 3 cycloadduct is preferably provided directly from the pressurizing step, as has been previously described and as is generally illustrated by Reaction Scheme I. That is, the FIG. 3 cycloadduct may be provided from the mixture of FIGS. 3 and 4 cycloadduct isomers obtained from the high pressure cycloaddition.

A suitable catalyst for the one step saturation and desulfurization is, for example, Raney nickel. Thus, the mixture of isomers obtained directly from the high pressure cycloaddition illustrated by Reaction Scheme I may be reduced and desulfurized over Raney nickel, as herebelow described, and as generally illustrated by Reaction Scheme II. Also illustrated by Reaction Scheme II, the reduction and desulfurization of the FIG. 4 cycloadduct of this mixture yields an isomeric cantharidin. The isomeric cantharidin is a novel compound, is believed to exhibit closely related properties to those of cantharidin, and accordingly will probably find similar applications.

A suitably volatile liquid is mixed with the mixture of isomers (having the FIG. 3 cycloadduct therein) and this mixture is then refluxed over the metallic catalyst. Reduction and desulfurization of the FIG. 3 cycloadduct (provided directly from the pressurizing step) over Raney nickel in refluxing ethyl acetate provides cantharidin, which may then be isolated in about 63% yield with respect to the 2,5-dihydrothiophene-3,4-dicarboxylic anhydride dienophile after one recrystallization in ethyl acetate. Such recrystallization of cantharidin separates it from isomeric cantharidin which remains in the mother liquor.

Reaction Scheme II

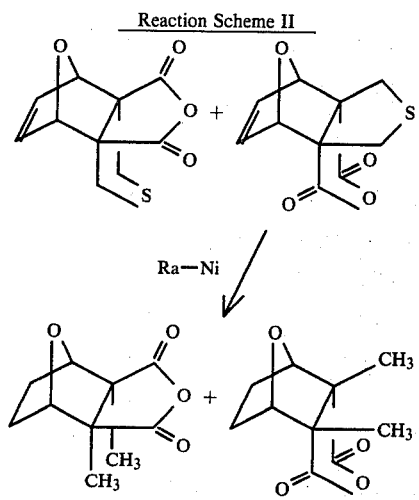

The reaction generally illustrated by Reaction Scheme II, above, may be facilitated by thermal activation, for example by heating to a temperature of about 65° C. during the contacting. Such heating depends upon the activity of the metallic catalyst, preferably Raney nickel, utilized in the contacting step. More active catalysts, for example very active types of Raney nickel, require little or no thermal activation. However, it has been observed that the FIG. 3 cycloadduct isomer decomposes in less than about 15 minutes at temperatures of about 200° C., so high temperatures during the contacting are not desirable.

Isomeric cantharidin is formed along with cantharidin, as illustrated by Reaction Scheme II, when the mixture of isomers (FIGS. 3 and 4 cycloadducts) from the pressurization is passed over Raney nickel. However, in the best mode contemplated for producing isomeric cantharidin, the FIG. 4 cycloadduct is preferably first separated from the FIG. 3 cycloadduct (by means such as chromatography on silica gel). The FIG. 4 cycloadduct may then be contacted with a metallic catalyst sufficient to perform a one-step desulfurization and saturation of the carbon-carbon double bond, e.g., forming isomeric cantharidin.

An alternative, method for producing cantharidin in accordance with the present invention may be by means of an intermediate cycloadduct, which is represented by FIG. 5, below.

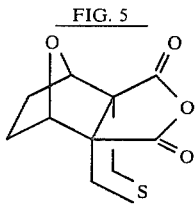

FIG. 5

The FIG. 5 cycloadduct is a novel compound and is characterized by the data of Table III, below.

TABLE III

Cycloadduct (FIG. 5)

m.p. 154–155° C. (acetone-hexane)
IR (CDCl$_3$) 1850, 1780, 1260, 1240, 970 cm$^{-1}$
NMR (CDCl$_3$, TMS) δ 1.7–2.2 (m,4), 2.79–3.13
    (AB$_2$, 4, δ$_1$ = 2.89, δ$_2$ = 3.04,
    J = 12.5), 4.73 (br.t,2, J = 3)
Anal. Calcd. for C$_{10}$H$_{10}$O$_4$S: C, 53.09;
    H, 4.46; S, 14.17
Found: C, 53.18; H, 4.51; S, 14.14

The FIG. 5 cycloadduct may be prepared by separating the FIG. 3 cycloadduct (by means such as chromatography on silica gel) from the FIG. 4 cycloadduct following the high pressure cycloaddition previously discussed. The FIG. 3 cycloadduct may then be hydrogenated in the pressure of a catalyst to saturate the carbon-carbon double bond. For example, the FIG. 3 cycloadduct quantitatively yields the FIG. 5 cycloadduct when hydrogenated over 10 mole percent of 10% paladium-carbon.

The FIG. 5 cycloadduct may be desulfurized to form cantharidin as a product therefrom, by means such as contacting the FIG. 5 cycloadduct with a metallic catalyst, for example Raney nickel.

In summary, the present invention provides a plurality of new cycloadduct compounds which are useful precursors in a commercially feasible, total synthesis of cantharidin on a large scale.

We claim:

1. A method of forming a cycloadduct comprising the steps of:
providing a dienophile having a maleic anhydride nucleus and a bridge substituted thereon, said dienophile of the structure

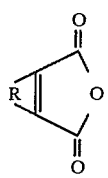

wherein R is said bridge, said bridge including a sulfur moiety for reducing an electron density of the carbon-carbon double bond of said maleic anhydride nucleus;
contacting said dienophile with furan to form a reaction solution of said dienophile and furan; and,
pressurizing said reaction solution to cause a cycloaddition between said dienophile and furan.

2. The method as in claim 1 wherein said sulfur moiety is a sulfide, sulfone or sulfoxide.

3. The method as in claim 1 wherein said bridge is —CH$_2$—S—CH$_2$—.

4. The method as in claim 3 wherein the contacting is in the presence of a solvent for said dienophile.

5. The method as in claim 1 wherein the pressurizing is at least about 1×10$^5$ kPa.

6. The method as in claim 1 wherein the pressurizing is from about 1×10$^5$ kPa to about 15×10$^5$ kPa.

7. A compound of the structure

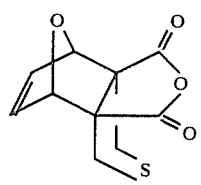

8. A compound of the structure

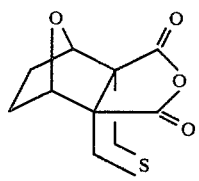

9. A method for producing cantharidin comprising the steps of:
providing a cycloadduct of the structure

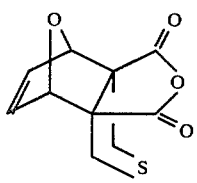

and contacting said cycloadduct with a catalyst sufficient to form cantharidin as a product therefrom.

10. The method as in claim 9 wherein said catalyst is Raney nickel.

11. The method as in claim 9 wherein the providing step includes saturating the carbon-carbon double bond of said cycloadduct to form another cycloadduct of the structure

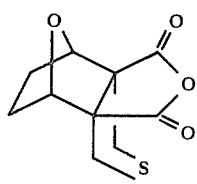

and wherein the contacting step includes contacting said another cycloadduct with a metallic catalyst sufficient to desulfurize said another cycloadduct and to form cantharidin as a product therefrom.

12. A method for producing cantharidin comprising the steps of:
providing a dienophile of the structure

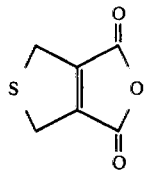

contacting said dienophile with furan to form a reaction solution;
pressurizing said reaction solution at a sufficient pressure to cause formation of a cycloadduct of the structure

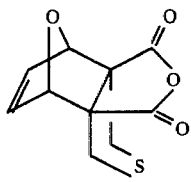

and thereafter reducing and desulfurizing said cycloadduct to form cantharidin.

13. The method as in claim 12 wherein said sufficient pressure is at least about $1 \times 10^5$ kPa.

14. The method as in claim 12 wherein the reducing and desulfurizing step includes refluxing said cycloadduct over Raney nickel.

15. The method as in claim 12 further comprising: isolating cantharidin following the reducing and desulfurizing step.

16. A method for producing an isomeric cantharidin comprising the steps of:
providing a dienophile of the structure

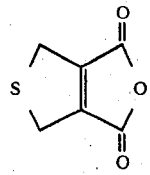

contacting said dienophile with furan to form a reaction solution;
pressurizing said reaction solution at a sufficient pressure to cause formation of a cycloadduct of the structure

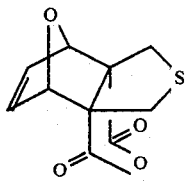

and thereafter reducing and desulfurizing said cycloadduct to form said isomeric cantharidin.

* * * * *

UNITED STATES PATENT AND TRADEMARK OFFICE
CERTIFICATE OF CORRECTION

PATENT NO. : 4,298,752

DATED : November 3, 1981

INVENTOR(S) : William G. Dauben et al.

It is certified that error appears in the above—identified patent and that said Letters Patent is hereby corrected as shown below:

Column 2, line 41, please change "aromatically" to --aromaticity--.

Column 4, Table I, under Fig. 3, please change "1885" to --1855--.

Signed and Sealed this

Second Day of March 1982

[SEAL]

Attest:

GERALD J. MOSSINGHOFF

Attesting Officer

Commissioner of Patents and Trademarks